United States Patent [19]

Kikuchi et al.

[11] Patent Number: 5,187,166

[45] Date of Patent: Feb. 16, 1993

[54] AZABICYCLO DERIVATIVES AND THEIR USE AS ANTIEMETICS

[75] Inventors: Haruhiko Kikuchi; Hiroaki Satoh; Nobuhiro Yahata; Koichiro Hagihara, all of Saitama; Toru Hayakawa, Kawagoe; Setsuko Mino, Fujimi; Makoto Yanai, Saitama, all of Japan

[73] Assignee: Nisshin Flour Milling Co., Ltd., Tokyo, Japan

[21] Appl. No.: 730,699

[22] Filed: Jul. 16, 1991

[30] Foreign Application Priority Data

Jul. 31, 1990 [JP] Japan ................ 2-201453
Oct. 31, 1990 [JP] Japan ................ 2-292000
Dec. 28, 1990 [JP] Japan ................ 2-418549
Mar. 26, 1991 [JP] Japan ................ 3-84473

[51] Int. Cl.$^5$ ............ A61K 31/54; A61K 31/535; A61K 31/495; A61K 31/50
[52] U.S. Cl. .................... 514/249; 514/224.2; 514/230.5; 544/349; 544/47; 544/105
[58] Field of Search .............. 544/349, 105, 47; 514/249, 230.5, 224.2

[56] References Cited

U.S. PATENT DOCUMENTS

| | | | |
|---|---|---|---|
| 2,970,144 | 1/1961 | Zirkle .................... | 544/105 |
| 4,352,802 | 10/1982 | Blaney .................... | 544/105 |
| 4,789,673 | 12/1988 | Donatsch et al. ........... | 514/214 |
| 4,800,225 | 1/1989 | Smith ..................... | 546/112 |
| 4,803,199 | 2/1989 | Donatsch et al. ........... | 514/214 |
| 4,910,207 | 3/1990 | Donatsch et al. ........... | 514/305 |

FOREIGN PATENT DOCUMENTS

| | | |
|---|---|---|
| 0096524 | 12/1983 | European Pat. Off. . |
| 0102195 | 3/1984 | European Pat. Off. . |
| 0377967 | 7/1990 | European Pat. Off. . |
| 2152049 | 7/1985 | United Kingdom . |
| 2153821 | 8/1985 | United Kingdom . |
| 2208862 | 4/1989 | United Kingdom . |
| 2231264 | 4/1990 | United Kingdom . |
| 2231265 | 4/1990 | United Kingdom . |

OTHER PUBLICATIONS

Nikitskaya et al., "Synthesis of 7-hydroxy-9-methyl-3,9-diazabicyclo [3.3.1]nonane and some derivatives", Chemical Abstracts, vol. 62 (1965) 14678d.
The New England Journal of Medicine, vol. 305, No. 16, Oct. 15, 1981, pp. 905-909, R. J. Gralla et al., "Antiemetic Efficacy of High-Dose Metoclopramide: Randomized Trials with Placebo and Prochlorperazine in Patients with . . .".
The Lancet, Jun. 27, 1987, vol. 1, No. 8548, pp. 1461-1463, D. Cunningham, et al., "Prevention of Emesis in Patients Receiving Cytotoxic Drugs by GR380321, a Selective 5-HT$_3$ Receptor Antagonist".
Chem. Pharm. Bull., vol. 19, No. 8, 1971, pp. 1696-1699, M. Murakami, et al., "An Improved Synthesis of Metoclopramide".
J. Org. Chem., vol. 23, Apr. 1958, p. 621, R. F. Smith, et al., "Diindazolo[2,3-α, 2',3'-d]Pyrazine-7,14-Dione".
J. Org. Chem., 26, Feb. 1961, pp. 395-407, C. L. Zirkle, et al., "The Isomeric 3-Oxa- and 3-Thia-granatanin-7-Ols and Their Derivatives; Reduction of Bicyclic Amino Ketones Related to Tropinone[1,2]".
Physiological Reviews, vol. 53, No. 1, Jan. 1973, A. S. Paintal, "Vagal Sensory Receptors and Their Reflex Effects", pp. 159-210.
Nature, vol. 316, Jul. 11, 1985, pp. 126-131, B. P. Richardson, et al., "Identification of Serotonin M-Receptor Subtypes and Their Specific Blockade by a New Class of Drugs".

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

Azabicyclo derivatives of formula (I) and pharmaceutically acceptable salts thereof:

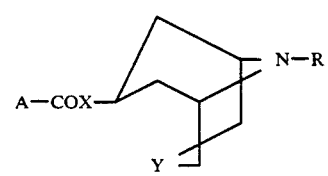

(I)

wherein A is a group of formula (a), (b) or (c):

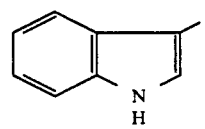

(a)

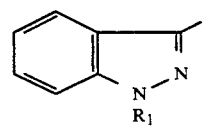

(b)

or

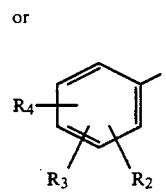

(c)

wherein
R$_1$ is hydrogen, C$_1$-C$_{10}$ alkyl, aralkyl or di(C$_1$-C$_4$) alkylamino(C$_1$-C$_6$)alkyl;
R$_2$, R$_3$ and R$_4$ may be the same or different and each is hydrogen, amino, halogen, C$_1$-C$_4$ alkoxy or phthalimide; X is O or NH;
R is C$_1$-C$_4$ alkyl; and
Y is NR, O or S;

having 5-HT$_3$ receptor antagonist activity.

5 Claims, No Drawings

AZABICYCLO DERIVATIVES AND THEIR USE AS ANTIEMETICS

FIELD OF THE INVENTION

This invention relates to new azabicyclo derivatives, processes for their preparation and to the pharmaceutical use thereof. In particular the invention relates to 3,9-diaza-, 3-oxa- or 3-thia-9-azabicyclo[3.3.1]nonane derivatives or pharmaceutically acceptable salts thereof which are selective antagonists of 5-HT (serotonin) at 5-HT$_3$ receptors.

BACKGROUND OF THE INVENTION

Nausea and vomiting are serious problems frequently observed in patients receiving a cancer chemotherapeutic agent and radiotherapy. Therefore control of nausea and vomiting is a very important auxiliary treatment for undergoing satisfactory treatment for cancer. Gralla, R. J. et al have reported in N. Engl. J. Med. 305, 905–909 (1981) that nausea and vomiting are effectively prevented by intravenous administration of metoclopramide at high dose. However it has been revealed that presently available antiemetics, particularly compounds containing a benzamide structure are associated with adverse reactions such as sedation, ataxia, diarrheas and tasikinesia due to their dopamine-blocking activities and central nervedepressant activities.

Cunningham, D. et al have reported in The Lancet, 1, 1461–1463 (1987) that specific antogonists of 5-HT$_3$ receptors prevent vomiting and nausea associated with cancer therapy. Thus 5-HT$_3$ receptor antagonists are believed to be anti-emetics which can prevent vomiting and nausea at a lower dose than known agents without adverse reactions associated.

As 5-HT$_3$ receptor antagonists, compounds containing an azabicyclic moiety are known as disclosed in U.S. Pat. Nos. 4,789,673; 4,803,199; 4,910,207; GB 2152049 A; U.S. Pat. No. 4,800,225, GB 2208862 A and European Patent Application 0377967 A2 and compounds containing an imidazole moiety are known as disclosed in GB 2153821 A.

Under such circumstances, it has been desired to develop more selective antagonists of 5-HT at 5-HT$_3$ receptors.

DETAILED DESCRIPTION OF THE INVENTION

We have now found that new azabicyclo derivatives which are structurally different from the prior compounds and possess a selectively effective antagonism against the effect of 5-HT at 5-HT$_3$ receptors.

Thus the present invention provides in one aspect a compound of formula (I) or a pharmaceutically acceptable salt thereof

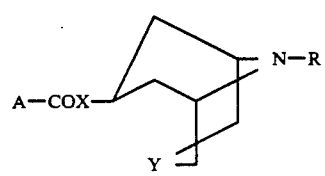
(I)

wherein A is a group of formula (a), (b) or (c):

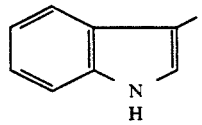
(a)

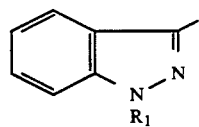
(b)

or

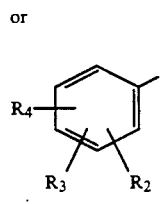
(c)

wherein
R$_1$ is hydrogen, C$_1$–C$_{10}$ alkyl, aralkyl or di(C$_1$–C$_4$)-alkylamino(C$_1$–C$_6$)alkyl; R$_2$, R$_3$ and R$_4$ may be the same or different and each is hydrogen, amino, halogen, C$_1$–C$_4$ alkoxy or phthalimide;
X is O or NH;
R is C$_1$–C$_4$ alkyl; and
Y is NR, O or S.

Examples of alkyl in R$_1$ and R include methyl, ethyl, n- and iso-propyl, n-, iso-, sec- and tert-butyl, n-and neo-pentyl, octyl, decyl or the like. Halogen includes fluorine, chlorine, bromine and iodine. Examples of aralkyl include benzyl, phenethyl and phenylpropyl. Examples of di(C$_1$–C$_4$)alkylamino include dimethylamino, diethylamino, di-n-propylamino, di-isopropylamino, di-n-butylamino, methylethylamino or the like. Examples of alkoxy includes methoxy, ethoxy, propoxy, butoxy or the like.

The pharmaceutically acceptable salts of the compounds of formula (I) include acid addition salts and quaternary ammonium salts. The acid addition salts refer to the compounds of formula (I) wherein a pharmaceutically acceptable organic or inorganic acid is added to a nitrogen atom at the 3- (in case of 3,9-diaza compounds) and/or 9-position. Those salts include hydrochloride, hydrobromide, hydroiodide, sulfate, phosphate, oxalate, maleate, fumarate, lactate, malate, citrate, tartrate, benzoate and methanesulfonate. The quaternary ammonium salts refer to the compounds of formula (I) which are quaternised at a nitrogen atom at the 3- (in case of 3,9-diaza compounds) and/or 9-position by a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p-toluenesulfonate.

The compounds of formula (I) and their pharmaceutically acceptable salts including acid addition salts and quaternary ammonium salts may form hydrates or solvates which are included within the scope of the invention.

The compounds of formula (I) can be prepared by a variety of processes based on known synthetic reaction. For instance 3,9-diaza-, 3-oxa- or 3-thia-9-azabicyclo[3.3.1]nonane derivatives of formula (I) are prepared by reacting an aromatic carboxylic or its reactive derivative of formula (II)

A—COOH    (II)

wherein A is as defined above, e.g., acid halides, esters such as alkyl and p-nitrophenyl esters, mixed acid anhydrides with acetic acid, with 3,9-diaza-, 3-oxa-or 3-thia-9-azabicyclo[3.3.1]nonane derivatives of formula (III)

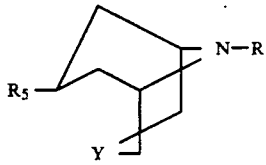

wherein R and Y are as defined above and R₅ is OH or NH₂.

The aromatic carboxylic acids or their reactive derivatives of formula (II) can be prepared by the processes as disclosed in Japanese Patent Kokai 48-81858, J. Org. Chem., 23, 621(1958) and Chem. Pharm. Bull., 19, 1696–1699 (1971). The compounds of formula (III) may be prepared in accordance with the process mentioned in J. Org. Chem., 26, 395(1961). Of these compounds 3,9-dimethyl-3,9-diazabicyclo[3.3.1]nonan-7-ol and 3,9-dimethyl-3,9-diazabicyclo[3.3.1]nonan-7-amine are new compounds not disclosed in any references. These two compounds can be prepared by hydrolysis of N,N-bis(2,2-dimethoxyethyl)methylamine, condensation with acetonedicarboxylic acid and methylamine to form 7-oxo-3,9-dimethyl-3,9-diazabicyclo-[3.3.1]nonane and reduction with lithium aluminum hydride to produce 3,9-dimethyl-3,9-diazabicyclo[3.3.1]nonan-7-ol or by reacting 7-oxo-3,9-dimethyl-3,9-diazabicyclo[3.3.1]nonane with hydroxylamine to form an oxime followed by amination of the oxime by catalytic reduction to produce 3,9-dimethyl-3,9-diazabicyclo[3.3.1]nonan-7-amine.

If an acid halide such as indole-3-carboxylic chloride is used as the reactive derivative of an aromatic carboxylic acid represented by formula (II), the reaction with the compounds of formula (III) is effected in a non-aqueous organic solvent at a temperature between −70° C. and a boiling point of the solvent. The organic solvents include diethyl ether, diisopropyl ether, tetrahydrofuran, dimethoxyethane, 1,4-dioxane, dimethylformamide and dimethyl sulfoxide. The reaction may be effected if necessary in the presence of an inorganic or organic acid binder such as triethylamine, tri-n-butylamine, pyridine, dimethylaniline, tetramethyl urea, metallic magnesium, n-butyl lithium, lithium diisopropyl amide, sodium amide, sodium hydride and metallic sodium. Subsequently, the reaction mixture is washed, extracted and purified to obtain the desired compounds of formula (I).

Alternatively, the compounds of formula (I) wherein A is a group of formula (b) can be prepared in accordance with the following reaction:

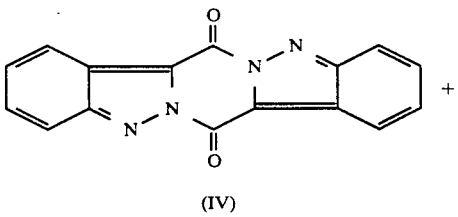

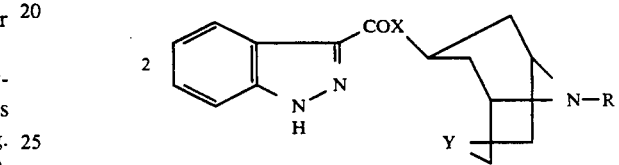

wherein R₅, X, Y and R are as defined above. As shown in the above reaction scheme, the desired compound of formula (I) can be produced by a reaction of diindazolo[2,3-a,2',3'-d]pyrazine-7,14-dione of formula (IV) (amidated dimer of 3-indazole carboxylic acid) with 3,9-diaza-, 3-oxa- or 3-thia-9-azabicyclo[3.3.1]nonane derivatives of formula (III). This reaction is usually carried out in an inert organic solvent at a temperature between room temperature and boiling point of the solvent in the presence of a catalyst catalyzing the reaction. The organic solvents used include ether solvents such as diethyl ether, diisopropyl ether, tetrahydrofuran, dimethoxyethane and 1,4-dioxane; ketone solvents such as acetone and methyl ethyl ketone; amide solvents such as dimethylformamide, diethylformamide and dimethylacetamide and dimethyl sulfoxide. The catalysts used include triethylamine, tri-n-butylamine, pyridine, dimethylaniline, sodium methoxide, sodium amide, sodium hydride, sodium hydroxide, potassium hydroxide, sodium carbonate and potassium carbonate.

The compounds of the invention may be isolated and purified in conventional manner.

Pharmaceutically acceptable salts of the compounds of formula (I) may be formed in conventional way. The acid addition salts may be formed for example by reaction of the base compound of formula (I) with a pharmaceutically acceptable inorganic acid such as hydrochloric, hydrobromic, hydroiodic, sulfuric and phosphoric acids or a pharmaceutically acceptable organic acid such as oxalic, maleic, fumaric, lactic, malic, citric, tartaric, benzoic and methanesulphonic acids. The quaternary ammonium salts may be formed in conventional way, e.g., by reaction of the compound of formula (I) with a lower alkyl halide such as methyl iodide, methyl bromide, ethyl iodide or ethyl bromide, a lower alkylsulfonate such as methyl methanesulfonate or ethyl methanesulfonate or a lower alkyl arylsulfonate such as methyl p-toluenesulfonate. The quarternization reaction can be effected in an organic solvent at a temperature between −20° C. and boiling point of the solvent. The organic solvents include diethyl ether, diisopropyl ether, tetrahydrofuran, dimethoxyethane, 1,4-dioxane, benzene, toluene, xylene, dimethylformamide and dimethyl sulfoxide. If a low boiling solvent such as diethyl ether or a low boiling reactant such as methyl chloride is used, the reaction is preferably carried out under pressure in a stainless closed tube. The reaction may be effected with no solvent.

Insofar as the preparation of any particular starting materials is not specifically described these are known or may be prepared in conventional manner.

The compounds of the present invention antagonize the action of 5-HT at 5-HT$_3$ receptors in the central nervous system and are useful in the treatment of psychotic disorders such as schizophrenia, mania, depression, anxiety, dementia, cognitive disorders and dependency on drugs as well as neurotic diseases such as migraine. The compounds of the invention antagonize the action of 5-HT at 5-HT$_3$ receptors in the peripheral nervous system and are useful in the treatment of gastric stasis symptoms of gastrointestinal dysfunction such as occur with dyspepsia, reflux oesophagitis, flatulence as well as gastrointestinal disorders such as gastritis, peptic ulcer, diarrhea occurred by various causes and Hirschsprung's disease. The present compounds are also in the treatment of nausea and vomiting, particularly that associated with cancer chemotherapy and radiotherapy.

The invention provides in another aspect a pharmaceutical composition having a selective antagonism of 5-HT at 5-HT$_3$ receptors, which comprises as an active ingredient an effective amount of a compound of formula (I), or a pharmaceutically acceptable salt thereof. Such compositions may be formulated in conventional manner using one or more pharmaceutically acceptable carriers and/or excipients.

The compounds of the invention can usually be administered orally or parenterally in the form of a pharmaceutical formulation. The pharmaceutical formulation includes tablets, capsules, suppositories, troches, syrups, creams, ointments, plasters, cataplasms, granules, powders, injections, suspensions and the like. It may be in bilayered or multilayered tablet with other drugs. The tablets may also be coated with a conventional coating to form, e.g., sugar-coated, enteric-coated or film-coated tablets.

In preparing solid formulations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, glycerin, polyethylene glycol, stearic acid, magnesium stearate and talc are employed.

A vegetable or synthetic wax or fat or a similar base is used in preparing the semi-solid formulations.

As additives in preparing the liquid formulations are used, for example, sodium chloride, sorbitol, glycerin, olive oil, almond oil, propylene glycol and ethyl alcohol.

The active ingredient is contained in the formulation in an amount of 0.001-100% by weight, suitably 0.01-50% by weight in the case of formulations for oral administration and 0.001-10% by weight in the case of formulations for injection based on the weight of the formulations.

Route and dosage of administration for the compounds of the invention are not specifically limited and are appropriately chosen depending upon form of the formulation, age and sex of the patient, severity of the disease and other factors. Daily dosage of the active ingredient is 0.01-1000 mg. No adverse toxicological effects are indicated at any of the above dosage ranges.

The following Examples illustrate the preparation of compounds of formula (I) and the following Preparative Examples illustrate the preparation of new intermediates.

PREPARATIVE EXAMPLE 1

N,N-bis(2,2-dimethoxyethyl)methylamine

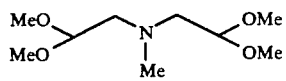

Potassium hydroxide (166 g, 2.96 mol) was dissolved in ethylene glycol (500 g) and to a solution was added under water cooling methylamine hydrochloride (50.0 g, 0.74 mol) and bromoacetaldehyde dimethylacetal (300 g, 1.78 mol). The solution was heated to reflux for 3 hrs. After completion of reaction, water (500 ml) was added to a reaction solution. The reaction solution was extracted with chloroform (500 ml×3), dried over anhydrous magnesium sulfate and concentrated under reduced pressure. The residue was separated by column chromatography ("Florisil" (silicagel) available from Wako Junyaku, Japan; hexane) to give the title compound (61 g).

b.p.: 80 85° C. (3 mmHg)

$^1$H-NMR (CDCl$_3$): δ 2.39 (s,3H), 2.63 (d,J=5 Hz,4H), 3.37 (s,12H), 4.50 (t,J=5 Hz)

PREPARATIVE EXAMPLE 2

7-Oxo-3,9-dimethyl-3,9-diazabicyclo[3.3.1]nonane

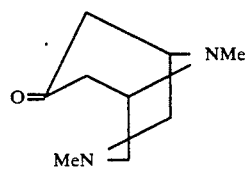

To N,N-bis(2,2-dimethoxyethyl)methylamine (61 g, 0.30 mol) was added distilled water (630 ml) and concentrated hydrochloric acid (101 ml, 1.21 mol) and a solution was heated to reflux for 1 hr. Subsequently, to the solution was added under ice-cooling an aqueous solution of sodium hydroxide (48.5 g sodium hydroxide, 200 ml water) (which was called "A solution"). On one hand, "A solution" was added at room temperature while stirring to an aqueous solution of disodium phosphate 12 hydrate (114.4 g) and citric acid (54.1 g) in water (709 ml) which was separately prepared. To a mixture were added acetone dicarboxylic acid (85.8 g, 0.59 mol) and methylamine hydrochloride (35.9 g, 0.53 mol). An aqueous sodium hydroxide solution was added to adjust the pH to 5 and the mixture was reacted for 15 hrs. To the reaction solution was added dropwise under ice-cooling concentrated hydrochloric acid (175 ml). The aqueous layer was washed with ethyl acetate (1000 ml×2) and sodium hydroxide (126 g) was added to the aqueous layer. The layer was extracted with chloroform (1000 ml×3), dried over anhydrous magnesium sulfate and concentrated under reduced pressure. The residue (23 g) was separated by column chromatography (Florisil, ethyl acetate) to give a crude product.

Recrystallization from hexane afforded the title compound (6.2 g).

m.p. 72°-73° C.

¹H-NMR (CDCl₃): δ 2.02 (d,J=13 Hz,1H), 2.20 (s,3H), 2.29 (s,1H), 2.43 (dd,J=2 Hz, J'=11 Hz,2H), 2.48-2.63 (m,2H), 2.58 (s,3H), 2.63-2.82 (m,2H), 3.13-3.22 (m,2H)

IR (KBr): 2950, 2920, 2790, 2760, 1719, 1702, 1462, 1343, 1264, 1203, 1182, 1078, 820 cm⁻¹

PREPARATIVE EXAMPLE 3

Endo-3,9-dimethyl-3,9-diazabicyclo[3.3.1]nonan-7-ol

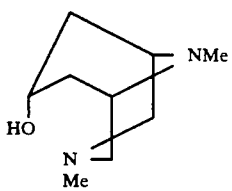

To a suspension of lithium aluminum hydride (0.95 g, 25.0 mmol) in dry THF (40 ml) was added dropwise at room temperature while stirring a solution of 7-oxo-3,9-dimethyl-3,9-diazabicyclo[3.3.1]nonae (2.78 g, 16.5 mmol) in dry THF (50 ml). After stirring at room temperature for 4.5 hrs, water (1 ml), 40% aqueous sodium hydroxide solution (1 ml) and water (3 ml) were added successively to a reaction solution. Further anhydrous magnesium sulfate was added and stirred, and thereafter the reaction was filtered. The filtrate was concentrated under reduced pressure to afford the title compound (2.62 g) as an oily product.

¹H-NMR (CDCl₃): δ 1.53 (d,J=15 Hz,2H), 2.25-2.55 (m,3H), 2.32 (s,3H), 2.46 (s,3H), 2.63 (d,J=11 Hz,2H), 2.79-2.92 (m,2H), 3.51 (d,J=5 Hz,1H), 3.75-3.90 (m,1H), 8.60 (d,J=8 Hz,1H).

PREPARATIVE EXAMPLE 4

Endo-3,9-dimethyl-3,9-diazabicyclo[3.3.1]nonan-7-amine

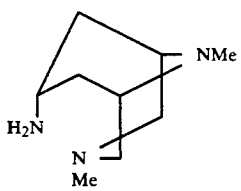

To a solution of 7-oxo-3,9-dimethyl-3,9-diazabicyclo[3.3.1]nonane (11.3 g, 67.2 mmol) in ethanol (130 ml) were added pyridine (12 ml) and hydroxylamine hydrochloride (4.81 g, 69.2 mmol) and a mixture was heated to reflux for 30 minutes. After completion of reaction, potassium carbonate (25.5 g) and water (12.6 ml) were added and the mixture was stirred for 2 hrs. After distilling off ethanol, the reaction mixture was extracted with chloroform (100 ml×3) and concentrated under reduced pressure to give the oxime (10.8 g) as crystals.

Subsequently, the resultant oxime (2.79 g, 15.2 mmol) was dissolved in ethanol (30 ml) and hydrogenated with Raney nickel at 70° C. at 50 kg/cm² for 24 hrs. in the presence of ammonium acetate (15 g). A reaction mixture was filtered and the filtrate was concentrated under reduced pressure to afford the title compound (2.27 g) as an oily product.

Oxime

¹H-NMR (CDCl₃): δ 2.16 (s,3H), 2.20-2.46 (m,5H), 2.51 (s,3H), 2.55-2.73 (m,2H), 2.92-3.07 (m,3H), 7.30-7.80 (br,1H) IR (KBr): 2940, 2800, 1455, 1175, 1080, 950, 760 cm⁻¹

Amine

¹H-NMR (CDCl₃): δ 1.34 (d,J=15 Hz,2H), 2.25 (s,3H), 2.46 (s,3H), 2.20-2.50 (m,5H), 2.58 (d,J=11 Hz,2H), 2.73-2.86 (m,2H), 2.70-3.20 (br,2H), 3.08 (t,J=7 Hz,1H).

PREPARATIVE EXAMPLE 5

Exo-3,9-dimethyl-3,9-diazabicyclo[3.3.1]nonan-7-amine

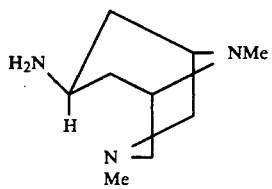

To a suspension of lithium aluminum hydride (1.91 g, 50.3 mmol) in THF (50 ml) was added dropwise at room temperature over a period of 30 minutes a solution of the oxime prepared in Preparative Example 4 (4.59 g, 25.1 mmol) in THF (150 ml). Then a mixture was stirred at room temperature for 1.5 hrs and heated to reflux for 1 hr. Water (5 ml), 10% aqueous sodium hydroxide solution (5 ml) and additional water (15 ml) were added to a reaction solution and stirred. To the reaction solution was added anhydrous magnesium sulfate and dried. Filtration and concentration under reduced pressure of the reaction solution gave the title compound (3.17 g) as a yellow liquid.

¹H-NMR (CDCl₃): δ 1.63 (d,J=15 Hz,2H), 2.15 (s,3H), 2.42 (s,3H), 2.00-2.50 (m,7H), 2.57-3.10 (m,3H), 3.50-3.75 (m,1H)

IR (neat): 3178, 2928, 2844, 2796, 1462, 1447, 1247, 1174, 1075, 803 cm⁻¹

EXAMPLE 1

(Endo-9-methyl-3-thia-9-azabicyclo[3.3.1]non-7-yl) 1H-indole-3-carboxylate

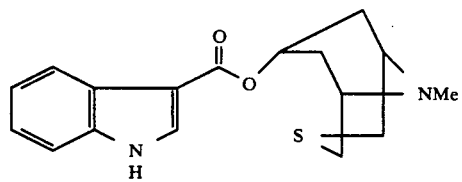

To a solution of endo-9-methyl-3-thia-9-azabicyclo[3.3.1]nonan-7-ol (0.70 g, 4.0 mmol) and tributylamine (0.75 g, 4.0 mmol) in dimethylformamide (5 ml) was added 1H-indole-3-carboxylic acid chloride (1.45 g, 8.1 mmol) and stirred at 110°-130° C. for 5.5 hrs. The reaction solution was cooled to room temperature and concentrated under reduced pressure. Water (15 ml) was added to the residue and powdered potassium carbonate was added until the solution was saturated. The aqueous layer was extracted with ethyl acetate (150 ml) and taken into diluted hydrochloric acid (150 ml). Then the diluted hydrochloric acid layer was washed with ethyl acetate, adjusted the pH to 10 with powdered potassium carbonate and extracted with chloroform (100 ml). The extract was dried over anhydrous sodium carbonate and concentrated under reduced pressure. Crystallization of the concentrate from a mixed solution of chloroform and hexane gave the title compound (0.52 g, 41% yield) as a colorless product.

m.p. 242° C.

$^1$H-NMR (DMSO-d$_6$): 1.62 (br.d,J=11.7 Hz,2H), 2.04 (t,J=10.3 Hz,2H), 2.05 (t,J=12.5 Hz,2H), 2.42–2.57 (m,2H), 2.45 (s,3H), 3.20–3.39 (m,4H), 5.20–5.37 (m,1H), 7.16–7.27 (m,2H), 7.45–7.52 (m,1H), 8.00–8.08 (m,2H), 11.85–11.95 (br.s,1H)

IR(KBr): 3248, 2924, 1683, 1664, 1534, 1443, 1329, 1315, 1171, 1040, 754 cm$^{-1}$

EXAMPLE 2

(Endo-9-methyl-3-oxa-9-azabicyclo[3.3.1]non-7-yl) 1H-indole-3-carboxylate

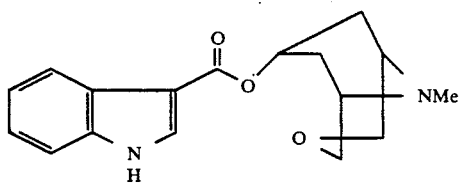

The title compound was prepared in 41% yield as colorless crystals by a similar way as in Example 1 from the reaction between endo-9-methyl-3-oxo-9-azabicyclo[3.3.1]-nonan-7-ol and 1H-indole-3-carboxylic acid chloride.

m.p. 197°–199° C.

$^1$H-NMR (CDCl$_3$): 1.79 (br.d,J=14.2 Hz,2H), 2.42–2.53 (m,2H), 2.56(s,3H), 2.70 (br.d,J=6 Hz,2H), 3.74 (d,J=11.0 Hz,2H), 4.01 (br.d,J=10.7 Hz,H), 5.40–5.50 (m,1H), 7.21–7.30 (m,2H), 7.35–7.42 (m,2H), 8.01 (d,J=2.4 Hz,1H), 8.27–8.32 (m,1H), 8.85–8.95 (br.s,1H)

IR(KBr): 3246, 2844, 1684, 1662, 1531, 1449, 1312, 1183, 1129, 1105, 1038, 751 cm$^{-1}$

EXAMPLE 3

(Endo-9-methyl-3-thia-9-azabicyclo[3.3.1]non-7-yl) 1-methylindazole-3-carboxylate

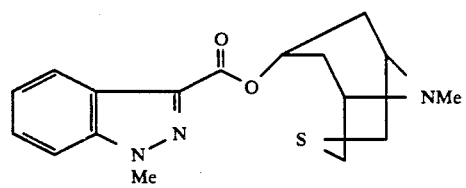

The title compound was prepared as colorless crystals by a similar way as in Example 1 from the reaction between endo-9-methyl-3-tia-9-azabicyclo[3.3.1]nonan-7-ol and 1-methylindazole-3-carboxylic acid chloride.

m.p. ca. 250° C. (dec.)

$^1$H-NMR (DMSO-d$_6$): 1.63 (d,J=12.5 Hz,2H), 2.10 (t,J=10.0 Hz,1H), 2.12 (t,J=10.0 Hz,1H), 2.40–2.60 (m,2H), 2.47 (s,3H), 3.23–3.40 (m,4H), 4.18 (s,3H), 5.39 (m,1H), 7.34 (t,J=7.6 Hz,1H), 7.49 (t,J=8.3 Hz, 1H), 7.74 (d,J=8.5 Hz,1H), 8.09 (d,J=8.1 Hz)

IR(KBr): 2935, 1716, 1480, 1430, 1355, 1260, 1210, 1205, 1160, 1105, 1035, 735 cm$^{-1}$

EXAMPLE 4

(Endo-9-methyl-3-oxa-9-azabicyclo[3.3.1]non-7-yl) 1-methylindazole-3-carboxylate

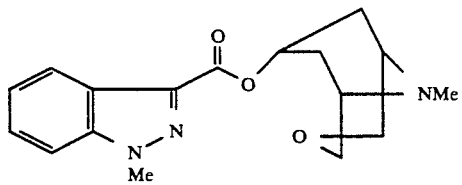

The title compound was prepared as colorless crystals by a similar way as in Example 1 from the reaction between endo-9-methyl-3-oxa-9-azabicyclo[3.3.1]nonan-7-ol and 1-methylindazole-3-carboxylic acid chloride.

m.p. 148°–149° C.

$^1$H-NMR (CDCl$_3$): 1.76–2.00 (m,2H), 2.40–2.88 (m,4H), 2.56(s,3H), 3.66–3.80 (m,2H), 3.88–4.08 (m,2H), 4.17 (s,3H), 5.50–5.68(m,1H), 7.20–7.36 (m,1H), 7.36–7.56 (m,1H), 8.43 (d,J=8.1 Hz,1H)

IR(KBr): 2950, 2890, 1720, 1210, 1185, 1175, 1130, 1115, 982, 757 cm$^{-1}$

EXAMPLE 5

(Endo-9-methyl-3-thia-9-azabicyclo[3.3.1]non-7-yl) 4-amino-5-chloro-2-methoxy benzoate

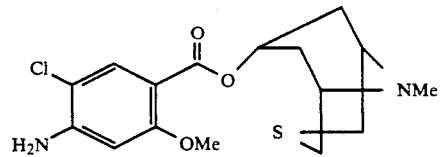

The title compound was prepared by a similar way as in Example 1 from the reaction between endo-9-methyl-3-thia-9-azabicyclo[3.3.1]nonan-7-ol and 4-amino-5-chloro-2-methoxybenzoic acid chloride.

$^1$H-NMR (CDCl$_3$): 1.50–1.80 (m,2H), 2.00–2.17 (m,2H), 2.44–2.61 (2H,m), 2.50 (s,3H), 3.20–3.40 (m,4H), 3.86 (s,3H), 4.35–4.48 (br., 2H), 5.25–5.45 (m,1H), 6.29 (s,1H), 7.87 (m,1H)

IR(KBr): 3350, 1700, 1630, 1250, 1230 cm$^{-1}$

EXAMPLE 6

Endo-9-methyl-3-thia-9-azabicyclo[3.3.1]non-7-yl 1H-indole-3-carboxamide

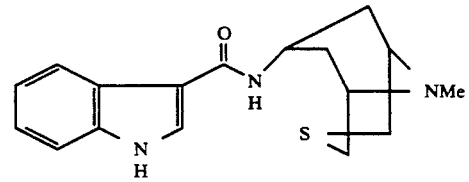

To a solution of indole-3-carboxylic acid chloride (2.64 g, 14.7 mmol) in a dry chloroform (40 ml) was added dropwise at room temperature under ice-cooling over a period of 50 minutes a solution of endo-9-methyl-3-thia-9-azabicyclo[3.3.1]nonan-7-amine (2.53 g, 14.7 mmol) and triethylamine (1.50 g, 14.8 mmol) in chloroform (40 ml). After stirring at room temperature for 20 hrs, the reaction solution was poured into diluted hydrochloric acid (50 ml) and the aqueous layer was washed with ethyl acetate. The acidic aqueous layer was adjusted to pH above 11 with aqueous diluted alkali solution, extracted with chloroform (50 ml×3), dried over anhydrous magnesium sulfate and concentrated under reduced pressure to afford a crude product (1.9 g). The crude product was purified by silica gel column chromatography (20 g SiO$_2$; 9/1 chloroform/methanol) and recrystallized from ethyl acetate to give the title compound (0.50 g).

m.p. 203°–205° C.

$^1$H-NMR (CDCl$_3$+CD$_3$ OD): 1.63 (br.d,J=12.5 Hz,1H), 1.95 (m,3H), 2.60 (s,3H), 2.62–2.77 (m,1H), 3.30 (m,2H), 3.51 (br.s,2H), 4.53 (dd,J=10.2 Hz,J'=2.9 Hz,1H), 4.65–4.83 (m,1H), 7.06 (br.d,J=12.0 Hz,1H), 7.18–7.22 (m,2H), 7.45 (m,1H), 8.06 (m,1H)

IR(KBr): 3440, 3180, 2930, 1635, 1540, 1505, 1455, 1320, 1200, 755 cm$^{-1}$

EXAMPLE 7

Endo-9-methyl-3-oxa-9-azabicyclo[3.3.1]non-7-yl 1H-indole-3-carboxamide

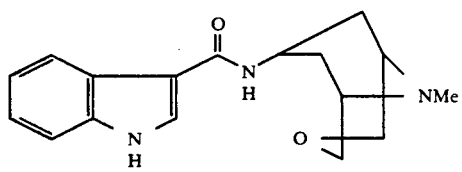

To a solution of endo-9-methyl-3-oxa-9-azabicyclo[3.3.1]nonan-7-amine (2.00 g, 12.8 mmol) in dry pyridine (20 ml) was added 4-dimethylaminopyridine (0.20 g, 1.6 mmol), to which was added dropwise under ice-cooling over a period of 15 minutes a solution of indole-3-carboxylic acid chloride (2.50 g, 13.9 mmol) in dry THF (10 ml). After stirring at room temperature for 11 hrs, the reaction solution was concentrated under reduced pressure. The residue to which toluene was added was again concentrated and extracted with aqueous diluted hydrochloric acid solution (30 ml). Then the aqueous layer was washed with ethyl acetate (30 ml), adjusted to pH above 11 with aqueous diluted sodium hydroxide solution and extracted with chloroform (50 ml×3). The organic layer was washed with water, dried over anhydrous magnesium sulfate and concentrated under reduced pressure to afford a crude product (2.10 g). Recrystallization from ethyl acetate gave the title compound (0.70 g) as colorless crystals.

m.p. 221°–223° C. (dec.)

$^1$H-NMR (CDCl$_3$+CD$_3$ OD): 1.70 (br.d,J=12.6 Hz,2H), 2.74(s,3H), 2.84 (m,4H), 3.62 (dd,J=12.0 Hz,J'=3.8 Hz,2H), 4.15–4.30 (m,2H), 4.85–4.95 (br.,1H), 7.17–7.27 (m,1H), 7.42–7.50 (m,1H), 7.80 (s,1H), 7.91–7.97 (m,1H), 8.65 (d,J=10.6 Hz,1H)

IR(KBr): 3395, 3225, 2925, 1610, 1535, 1435, 1330, 1180, 1100 cm$^{-1}$

EXAMPLE 8

Endo-9-methyl-3-oxa-9-azabicyclo[3.3.1]non-7-yl 5-chloro-2-methoxy-4-phthalimide phenylcarboxamide

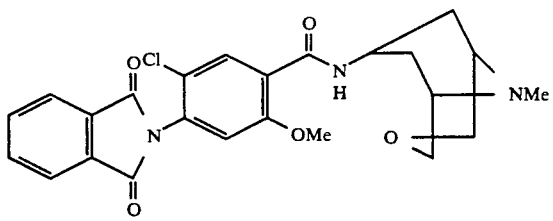

The title compound was prepared by a similar way as in Example 6 from the reaction between endo-9-methyl-3-oxa-9-azabicyclo[3.3.1]nonan-7-amine and 5-chloro-2-methoxy-4-phthalimide acid chloride.

$^1$H-NMR (CDCl$_3$): 1.50–1.70 (m,2H), 2.76 (s,3H), 2.70–2.90(m,2H), 3.57 (m,2H), 3.89 (s,3H), 3.80–4.20 (m,4H), 4.90–5.05 (m,1H), 6.94 (s,1H), 7.75–7.90 (m,2H), 7.90–8.03 (m,2H), 8.36 (s,1H), 9.45 (d, J=Hz,1H)

IR (film): 3330, 2940, 2870, 1750, 1650, 1500, 1390, 1270, 1110, 760, 730 cm$^{-1}$

EXAMPLE 9

(Endo-3,9-dimethyl-3,9-diazabicyclo[3.3.1]non-7-yl) 1H-indole-3-carboxylate

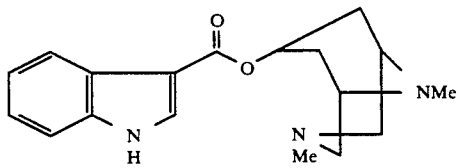

The title compound was prepared as colorless crystals by a similar way as in Example 1 from the reaction between endo-3,9-dimethyl-3,9-diazabicyclo[3.3.1]nonan-7-ol and 1H-indole-3-carboxylic acid chloride.

m.p. 197°–199° C.

$^1$H-NMR (CDCl$_3$): δ 1.77–1.91 (m,2H), 2.27 (s,3H), 2.28–2.66 (m,6H), 2.48 (S,3H), 2.91–3.03 (m,2H), 5.43 (quint,1H), 7.17–7.30 (m,2H), 7.34–7.44 (m,1H), 7.91 (d,1H), 8.22–8.32 (m,1H), 8.75–8.95 (br.,1H)

IR (KBr): 3198, 2928, 2784, 1660, 1439, 1313, 1187, 1042 cm$^{-1}$

EXAMPLE 10

(Endo-3,9-dimethyl-3,9-diazabicyclo[3.3.1]non-7-yl) 1-methylindazole-3-carboxylate

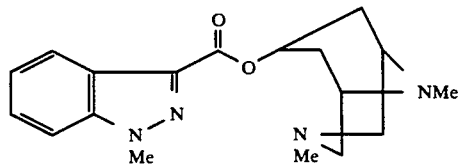

The title compound was prepared as colorless crystals by a similar way as in Example 7 from the reaction between endo-3,9-dimethyl-3,9-diazabicyclo[3.3.1]nonan-7-ol and 1-methylindazole-3-carboxylic acid chloride.

m.p. 240° C. (dec., hydrochloride)

$^1$H-NMR (CDCl$_3$): δ 1.86–2.06 (m,2H), 2.22 (s,3H), 2.28–2.76 (m,6H), 2.47 (s,3H), 2.92–3.08 (m,2H), 4.17 (s,3H), 5.42–5.64 (m,1H), 7.22–7.36 (m,1H), 7.38–7.50 (m,2H), 8.28 (d,J=8.06 Hz,1H)

IR(neat): 2940, 2800, 1720, 1483, 1270, 1220, 1122 cm$^{-1}$

EXAMPLE 11

Endo-3,9-dimethyl-3,9-diazabicyclo[3.3.1]non-7-yl 1H-indole-3-carboxamide

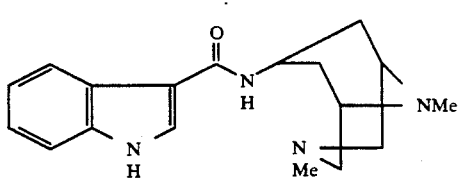

The title compound was prepared by a similar way as in Example 6 from the reaction between endo-3,9-dimethyl-3,9-diazabicyclo[3.3.1]nonan-7-amine and 1H-indole-3-carboxylic acid chloride.

m.p. 202°–204° C.

$^1$H-NMR (CDCl$_3$): δ 1.50 (br.d,2H), 2.19 (s,3H), 2.40–2.59 (m,4H), 2.52 (s,3H), 2.59–2.73 (m,2H), 2.80–2.90 (m,2H), 4.57–4.71 (m,1H), 7.14–7.25 (m,2H), 7.34–7.45 (m,1H), 7.57 (d,J=Hz,1H), 7.94–8.06 (m,1H), 9.60–9.73 (br.,1H), 10.20 (d,J=Hz,1H)

IR (KBr): 3160, 2930, 1605, 1535, 1445, 1250, 1210, 750 cm$^{-1}$

EXAMPLE 12

Endo-3,9-dimethyl-3,9-diazabicyclo[3.3.1]non-7-yl 1-methylindazole-3-carboxamide

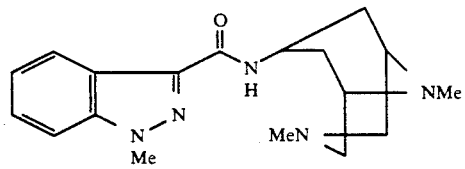

To a solution of the amine (1.40 g, 8.28 mmol) prepared in Preparative Example 4 dissolved in pyridine (30 ml) was added a catalytic amount of dimethylaminopyridine and subsequently 1-methylindazole-3-carboxylic acid chloride (1.60 g, 8.22 mmol). After stirring at room temperature for 16 hrs, the reaction solution was concentrated under reduced pressure. The aqueous layer the pH of which was adjusted to 1 with diluted hydrochloric acid was washed with ethyl acetate (50 ml×2). The aqueous layer the pH of which was adjusted to 11 or higher with sodium hydroxide was extracted with chloroform (100 ml×3), dried over anhydrous magnesium sulfate and concentrated under reduced pressure. The resultant residue was separated and purified by column chromatography (SiO$_2$: chloroform-ethanol). The resultant crude product was recrystallized from a mixed solvent of chloroform and hexane to afford the title compound (1.11 g).

m.p. 166°–167° C.

$^1$H-NMR (CDCl$_3$) δ1.48 (d,J=15 Hz,2H), 2.32–2.92(m,8H), 2.50(s,3H), 2.53 (s,3H), 4.07 (s,3H), 4.50–4.72 (m,1H), 7.16–7.30 (m,1H), 7.30–7.42 (m,2H), 8.41 (d,J=8 Hz,1H), 11.26 (d,J=10 Hz,1H)

IR (KBr) 2926, 2802, 1644, 1522, 1495, 1274, 1213, 788, 752 cm$^{-1}$

EXAMPLE 13

Endo-3,9-dimethyl-3,9-diazabicyclo[3.3.1]non-7-yl) 1H-indazole-3-carboxamide

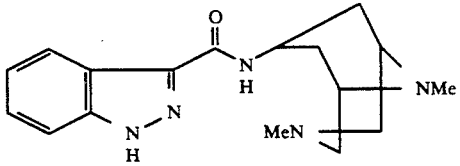

To a solution of the amine (1.40 g, 8.28 mmol) prepared in Preparative Example 4 dissoved in pyridine (40 ml) was added a catalytic amount of dimethylaminopyridine and subsequently 1H-indazole-3-carboxylic acid chloride (2.20 g, 12.2 mmol). After stirring at room temperature for 16 hrs, the reaction solution was concentrated under reduced pressure. The aqueous layer the pH of which was adjusted to 1 with diluted hydrochloric acid was washed with ethyl acetate (50 ml×2). The aqueous layer the pH of which was adjusted to 11 or higher with sodium hydroxide was extracted with chloroform (100 ml×3), dried over anhydrous magnesium sulfate and concentrated under reduced pressure. The resultant residue was separated and purified by column chromatography (SiO$_2$; chloroform-/ethanol). The resultant crude product was recrsytallized from a mixed solvent of chloroform and hexane to afford the title compound (0.40 g).

m.p. 256°–257° C.

$^1$H-NMR (CDCl$_3$-CD$_3$OD) δ 1.50 (d,J=15 Hz,2H), 2.35–3.00 (m,8H), 2.44 (s,3H), 2.52 (s,3H), 4.48–4.66 (m,1H), 7.14–7.56 (m,3H), 8.30 (d,J=8 Hz,1H), 11.35–11.55 (m,1H), 12.63 (bs,1H)

IR (KBr) 2924, 2810, 1642, 1505, 1476, 757 cm$^{-1}$

EXAMPLE 14

This Example illustrates the preparation of the compound of Example 13, i.e., endo-3,9-dimethyl-3,9-diazabicyclo[3.3.1]non-7-yl) 1H-indazole-3-carboxamide by a reaction of 3-indazole carboxylic acid dimer with the amine prepared in Preparative Example 4, i.e., endo-3,9-dimethyl-3,9-diazabicyclo[3.3.1]nonan-7-amine.

To a solution of the amine (8.59 g, 50.8 mmol) prepared in Preparative Example 4 dissolved in dimethylformamide (273 ml) was added under ice-cooling potassium carbonate (10.58 g) as a base. Then 4-dimethylaminopyridine (0.314 g) and 3-indazole carboxylic acid dimer (7.34 g, 25.5 mmol) were added. A reaction mixture was returned to room temperature and stirred for 24 hrs. The reaction mixture was concentrated under reduced pressure and then water was added. The precipitated crystals were collected by filtration and the resultant crude crystals were purified by column chromatography (silica gel; 20/1 CHCl$_3$/EtOH) to afford the end compound (9.54 g, 60% yield). This compound was converted to the hydroxide by conventional method.

EXAMPLE 15

Endo-3,9-dimethyl-3,9-diazabicyclo[3.3.1]non-7-yl 1-ethylindazole-3-carboxamide

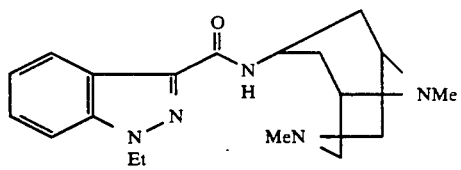

To a solution of the compound (0.800 g, 2.55 mmol) prepared in Example 14 dissolved in DMF (24 ml) was added under ice-cooling 60% sodium hydride (0.153 g, 3.83 mmol) and a mixture was stirred for 30 minutes. Then ethyl iodide (0.597 g, 3.83 mmol) was added under ice-cooling to the mixture which was stirred for 30 minutes. After additional stirring at room temperature for 6 hrs, water (40 ml) was added to the reaction mixture which was extracted with chloroform (50 ml×3). The organic layer was washed with saturated saline solution, dried over anhydrous magnesium sulfate and concentrated under reduced pressure. The residue (1.0 g) was separated and purified by silica gel column chromatography (SiO$_2$; chloroform/ethanol) to afford the title compound (0.79 g).

m.p. 145.5°–146.5° C.

$^1$H-NMR (CDCl$_3$) δ 1.38–1.62 (m,5H), 2.30–2.96(m,8H), 2.48(s,3H), 2.53 (s,3H), 4.43 (d,J=7 Hz,2H), 4.50–4.70 (m,1H), 7.14–7.30 (d,J=7Hz,1H), 11.1 (d,J=10 Hz,1H)

IR (KBr) 2930, 1648, 1526, 1467, 1267, 1205, 754 cm$^{-1}$

EXAMPLE 16

Endo-3,9-dimethyl-3,9-diazabicyclo[3.3.1]non-7-yl 1-(2-propyl)indazole-3-carboxamide

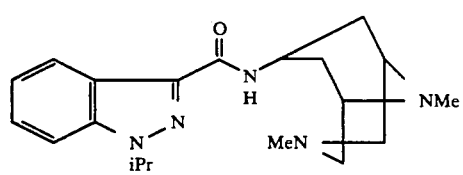

The title compound was prepared in accordance with the procedure mentioned in Example 15 from endo-3,9-dimethyl-3,9-diazabicyclo[3.3.1]non-7-yl 1H-indazole-3-carboxamide and isopropyl bromide.

m.p. 179°–180° C.

$^1$H-NMR (CDCl$_3$) δ1.50 (d,J=15 Hz,2H), 1.58 (s,3H), 1.61(s,3H), 2.30–2.96 (m,8H), 2.48 (s,3H), 2.53 (s,3H), 4.56–4.76 (m,1H), 4.76–4.96 (m,1H), 7.14–7.28 (m,1H), 7.28–7.48 (m,2H), 8.44 (d,J=8 Hz,1H), 10.8 (d,J=10 Hz,1H)

IR (KBr) 2930, 2798, 1641, 1521, 1489, 1454, 1267, 1194, 750 cm$^{-1}$

EXAMPLE 17

Endo-3,9-dimethyl-3,9-diazabicyclo[3.3.1]non-7-yl 1-benzylindazole-3-carboxamide

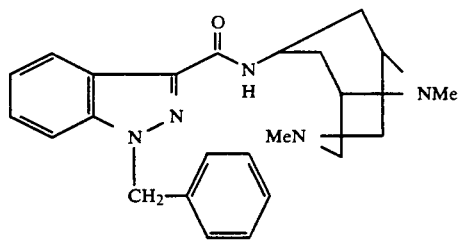

The title compound was prepared in accordance with the procedure mentioned in Example 15 from endo-3,9-dimethyl-3,9-diazabicyclo[3.3.1]non-7-yl 1H-indazole-3-carboxamide and benzyl bromide.

m.p. 153.5°–154.5° C.

IR (KBr) 2924, 2804, 1649, 1525, 1490, 1175, 753 cm$^{-1}$

EXAMPLE 18

Endo-3,9-dimethyl-3,9-diazabicyclo[3.3.1]non-7-yl 1-(n-octyl)indazole-3-carboxamide

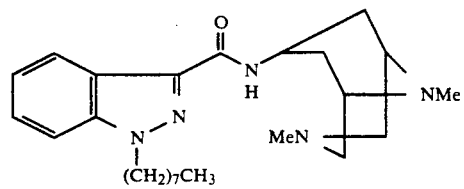

The title compound was prepared in accordance with the procedure mentioned in Example 15 from endo-3,9-dimethyl-3,9-diazabicyclo[3.3.1]non-7-yl 1H-indazole-3-carboxamide and n-octyl bromide.

IR (neat) 2926, 2854, 2800, 1648, 1517, 1489, 1460, 1268, 1176, 750 cm$^{-1}$ $n^{21.5}{}_D$=1.5481

EXAMPLE 19

Endo-3,9-dimethyl-3,9-diazabicyclo[3.3.1]non-7-yl 1-[2-(dimethylamino)ethyl]indazole-3-carboxamide

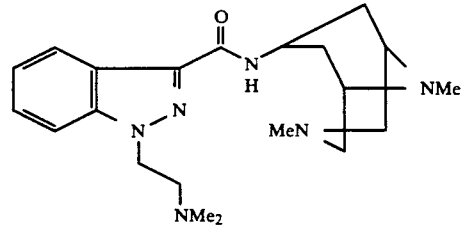

The title compound was prepared in accordance with the procedure mentioned in Example 15 from endo-3,9-dimethyl-3,9-diazabicyclo[3.3.1]non-7-yl 1H-indazole-3-carboxamide and 2-dimethylaminoethyl chloride.

IR (neat) 2930, 2798, 1652, 1518, 1491, 1460, 1267, 1214, 1175, 750 cm$^{-1}$ $n^{21.5}{}_D$=1.5554

EXAMPLE 20

Exo-3,9-dimethyl-3,9-diazabicyclo[3.3.1]non-7-yl 1H-indole-3-carboxamide

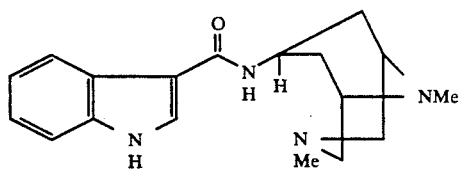

The title compound was prepared in accordance with the procedure described in Example 12 using exo-3,9-dimethyl-3,9-diazabicyclo[3.3.1]nonan-7-amine prepared in Preparative Example 5.

m.p. 219°–221° C.

$^1$H-NMR (CDCl$_3$): δ 1.71 (s,2H), 1.94–2.06 (m,2H), 2.23 (s,3H), 2.35–2.57 (m,4H), 2.60 (s,3H), 2.82–2.94 (m,1H), 3.51–3.61 (m,1H), 4.10 (d,J=9 Hz,1H), 5.30 (q,J=9 Hz,1H), 7.15–7.30 (m,2H), 7.30–7.42 (m,1H), 7.78 (d,J=3 Hz,1H), 8.15–8.25 (m,1H), 8.73–8.87 (br.,1H)

IR (KBr): 2920, 2975, 1650, 1455, 1175, 995, 750 cm$^{-1}$

EXAMPLE 21

Exo-3,9-dimethyl-3,9-diazabicyclo[3.3.1]non-7-yl 1-methylindazole-3-carboxamide

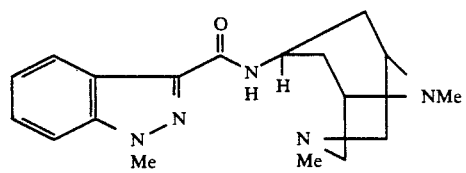

The title compound was prepared in accordance with the procedure described in Example 14 using exo-3,9-dimethyl-3,9-diazabicyclo[3.3.1]nonan-7-amine prepared in Preparative Example 5.

m.p. 175.5°–176.5° C.

IR (KBr) 2938, 2800, 1651, 1520, 1492, 1468, 1373, 1304, 1229, 1165, 748 cm$^{-1}$

EXAMPLE 22

Endo-3,9-dimethyl-3,9-diazabicyclo[3.3.1]non-7-yl 4-amino-5-chloro-2-methoxyphenylcarboxyamide

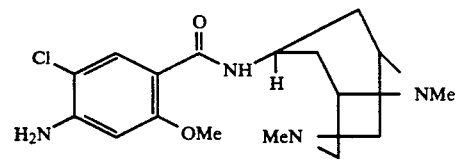

A solution of 5-chloro-2-methoxy-4-phenylcarboxychloride (3.98 g, 11.9 mmol) and endo-3,9-dimethyl-3,9-diazabicyclo[3.3.1]nonan-7-amine (11.9 mmol) in pyridine (60 ml) was reacted at room temprature for 20 hrs in the presence of a catalytic amount of N,N'-dimethylaminopyridine and treated in conventional manner. The resultant crude amide (about 2.19 g) to which was added in methanol (50 ml) hydrazine hydrate (0.233 g) at −20° C., was reacted at room temperature for 2 hrs, further heated to reflux for 1 hr and treated in usual manner. The resultant crude product was purified by silica gel column chromatography (40/1 chloroform/methanol) to afford the title compound (0.36 g, 1.02 mmol).

m.p. 266°–267° C.

$^1$H-NMR (CDCl$_3$): δ 1.43 (d,J=15.1 Hz,2H), 2.19 (s,3H), 2.30–2.72 (m,9H), 2.50 (s,3H), 2.82 (bs,2H), 3.81 (s,3H), 4.31 (s,2H), 4.44–4.66 (m,1H), 6.29(s,1H), 7.74 (s,1H), 9.97 (d,J=9.2 Hz,1H)

IR (KBr): 3314, 3208, 2934, 1625, 1589, 1526, 1501, 1212 cm$^{-1}$

Pharmacological Test on 5-HT$_3$ Receptor Antagonist Activity

Temporary bradycardia is induced by administration of 5-HT (serotonin) to anaesthetised rats via jugular vein (von Bezold Jarisch Reflex) (A. S. Paintal, Physiol. Rev., 53, 159–210 (1973)). Richardson B. P. et al have proved in Nature, 316, 126–131 (1985) that the 5-HT-induced reflex occurs through 5-HT$_3$ receptors. Thus the 5-HT$_3$ receptor antagonist activity of the present compounds can be demonstrated by inhibition of said reflex.

The compounds of the present invention were evaluated for antagonism of the von Bezold-Jarisch reflex induced by 5-HT in the anaesthetised rat according to the following method.

Rats were anaesthetised with urethane (1 g/kg, intraperitoneally) and blood pressure and heart rate recorded from left femoral artery. Percent inhibition was calculated from bradycardia induced by 5-HT (30 μg/kg) given 5 minutes following intrajugular administration of a compound of the invention, taking the bradycardia induced by the intrajugular administration of 5-HT. The compounds of the present invention were tested in the form of their hydrochloride salts. The results are shown below.

| Compounds of Example | Percent Inhibition (%) Concentration of test compound (μg/kg, i.v.) | | |
|---|---|---|---|
| | 0.1 | 1.0 | 10 |
| 1 | 51 | 85 | |
| 2 | 54 | 93 | |
| 3 | 43 | 67 | |
| 4 | 59 | 80 | |
| 5 | | | 58 |
| 7 | | 36 | 72 |
| 9 | 28 | 58 | 91 |
| 11 | | 39 | 79 |
| 12 | 25 | 71 | |
| 13 | | 28 | 95 |
| 15 | 42 | 91 | |
| 16 | 59 | | |
| 17 | 43 | 91 | |
| 18 | | 15 | |
| 19 | | 10 | |
| 22 | | 43 | 89 |

The following examples illustrate pharmaceutical formulations according to the invention.

| Tablets (per tablet) | |
|---|---|
| Compound of Example 1 | 1 mg |
| Lactose | 70 mg |
| Crystalline cellulose | 20 mg |
| Corn starch | 8 mg |
| Magnesium stearate | 1 mg |

The above ingredients were uniformly blended to prepare powders for direct compression. The powders were formed in a rotary tabletting machine to tablets each 6 mm in diameter and weighing 100 mg.

| Granules (per divided packet) | |
|---|---|
| Compound of Example 2 | 1 mg |
| Lactose | 99 mg |
| Crystalline cellulose | 50 mg |
| Corn starch | 50 mg |
| Hydroxypropylcellulose | 10 mg |
| Ethanol | 9 mg |

The compound, lactose, corn starch and crystalline cellulose were uniformly blended and a solution of hydroxypropylcellulose in ethanol was added. The mixture was kneaded and granulated by an extrusion granulation method. The granules were then dried in a drier at 50° C. The dried granules were screened to granule sizes between 297 μm and 1460 μm to give a granule formulation weighing 200 mg per divided packet.

| Syrups | |
|---|---|
| Compound of Example 5 | 0.100 g |
| Refined sugar | 30.000 g |
| D-sorbitol, 70 W/V % | 25.900 g |
| Ethyl paraoxybenzoate | 0.030 g |
| Propyl paraoxybenzoate | 0.015 g |
| Flavor | 0.200 g |
| Glycerin | 0.150 g |
| 96% Ethanol | 0.500 g |
| Distilled water | q.s. |

The compound, refined sugar, D-sorbitol, methyl paraoxybenzoate and propyl paraoxybenzoate were dissolved in 60 g of warm water. After cooling, glycerin and a solution of the flavor in ethanol were added. Distilled water was added to the mixture to make up a total amount of 100 ml.

| Injections | |
|---|---|
| Compound of Example 3 | 0.1 mg |
| Sodium chloride | 10 mg |
| Distilled water | q.s. |

The compound and sodium chloride were dissolved in distilled water to make up a total amount of 1.0 ml.

What is claimed is:

1. A compound of formula (I) or a pharmaceutically acceptable salt thereof:

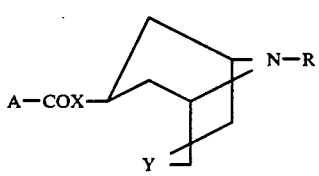

(I)

wherein A is of formula (a):

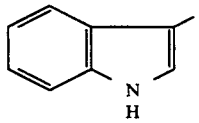

(a)

wherein
X is O or NH;
Y is NR; and
R is $C_1$–$C_4$ alkyl.

2. A compound of formula (I) or a pharmaceutically acceptable salt thereof:

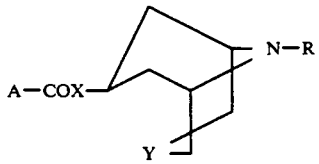

(I)

wherein A is of formula (b):

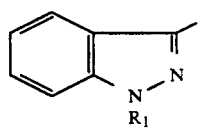

(b)

wherein
$R_1$ is hydrogen, $C_1$–$C_{10}$ alkyl, aralkyl or di($C_1$–$C_4$) alkylamino ($C_1$–$C_6$)alkyl;
X is O or NH;
Y is NR; and
R is $C_1$–$C_4$ alkyl.

3. A compound of formula (I) or a pharmaceutically acceptable salt thereof:

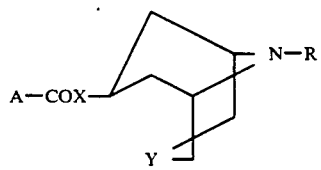

(I)

wherein A is of formula (c):

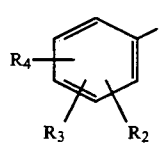

(c)

wherein
$R_2$, $R_3$ and $R_4$ may be the same or different and each is hydrogen, amino, halogen, $C_1$–$C_4$ alkoxy or phthalimide;
X is NH;
Y is NR; and
R is $C_1$–$C_4$ alkyl.

4. A pharmaceutical composition which comprises as an active ingredient a compound or a pharmaceutically acceptable salt thereof as defined in any one of claims 1 to 3 and a pharmaceutically acceptable carrier.

5. Process for the treatment of psychotic disorders, neurotic diseases, gastric stasis symptoms of gastrointestinal dysfunction, gastrointestinal disorders, nausea and vomiting, comprising administering to a subject in need of such treatment a compound as defined in any one of claims 1-3.

* * * * *